US008480408B2

(12) United States Patent
Ishii et al.

(10) Patent No.: US 8,480,408 B2
(45) Date of Patent: Jul. 9, 2013

(54) MEDICAL TRAINING MODEL DEVICE

(75) Inventors: Toku Ishii, Morioka (JP); Akio Doi, Morioka (JP); Kentaro Katamachi, Morioka (JP); Kyoko Noguchi, Morioka (JP); Hiroshi Uno, Tsuruoka (JP)

(73) Assignee: Koken Co., Ltd., Tokyo (JP)

( * ) Notice: Subject to any disclaimer, the term of this patent is extended or adjusted under 35 U.S.C. 154(b) by 1474 days.

(21) Appl. No.: 11/883,609

(22) PCT Filed: Feb. 8, 2006

(86) PCT No.: PCT/JP2006/302192
§ 371 (c)(1),
(2), (4) Date: Oct. 4, 2007

(87) PCT Pub. No.: WO2006/085564
PCT Pub. Date: Aug. 17, 2006

(65) Prior Publication Data
US 2008/0113324 A1    May 15, 2008

(30) Foreign Application Priority Data

Feb. 9, 2005  (JP) .................................. 2005-032614

(51) Int. Cl.
*G09B 23/28* (2006.01)
(52) U.S. Cl.
USPC ............................ 434/273; 434/272; 434/267
(58) Field of Classification Search
USPC .................. 434/262, 272, 275, 273, 267, 268
See application file for complete search history.

(56) References Cited

U.S. PATENT DOCUMENTS 4,439,162 A * 3/1984 Blaine ........................... 434/268
(Continued)

FOREIGN PATENT DOCUMENTS

| JP | 2000-506264 | 5/2000 |
| JP | 2002-511156 | 4/2002 |
| JP | 2004-348095 | 12/2004 |

OTHER PUBLICATIONS

International Search Report for PCT/JP2006/302192 dated Apr. 25, 2006.
(Continued)

*Primary Examiner* — Xuan Thai
*Assistant Examiner* — Peter Egloff
(74) *Attorney, Agent, or Firm* — Kilyk & Bowersox, P.L.L.C.

(57) ABSTRACT

[Problem] To provide a medical training simulation model having a display enabling training by a simulation model simulating the structure of an organism, and objective and visual recognition of the three-dimensional position of an inserted endoscope, a finger or the like in an organ or tissue. [Means for Solving the Problem] A teaching material model system having a teaching material model for clinical examination inside of an organism has a display screen creating device for creating the internal structure of an organism model formed of a nonmagnetic material by three-dimensional CG on a display screen, a specific signal transmitting device, and a sensor for detecting a signal from the specific signal transmitting device as constituting device, wherein the signal generated by the specific signal transmitting device is detected by the sensor, the signal detected by the sensor is transmitted to create a display screen by the display screen creating device, and the system is provided with a real time display device for displaying the positional situation of the sensor created on the display screen for the internal structure of a teaching material organism model displayed on the display screen by three-dimensional CG.

3 Claims, 3 Drawing Sheets

U.S. PATENT DOCUMENTS

| | | | |
|---|---|---|---|
| 4,988,981 A * | 1/1991 | Zimmerman et al. | 345/158 |
| 5,609,485 A * | 3/1997 | Bergman et al. | 434/262 |
| 5,803,738 A * | 9/1998 | Latham | 434/29 |
| 6,211,666 B1 | 4/2001 | Acker | |
| 6,336,812 B1 | 1/2002 | Cooper et al. | |
| 6,428,323 B1 * | 8/2002 | Pugh | 434/274 |
| 6,544,041 B1 * | 4/2003 | Damadian | 434/262 |
| 6,669,483 B1 * | 12/2003 | Leight et al. | 434/262 |
| 6,685,530 B1 * | 2/2004 | Rehkemper et al. | 446/175 |
| 6,863,536 B1 * | 3/2005 | Fisher et al. | 434/272 |
| 2006/0207381 A1 * | 9/2006 | Warner et al. | 74/513 |

OTHER PUBLICATIONS

Notification of Transmittal of Translation of the International Preliminary Report on Patentability (Chapter I or Chapter II of the Patent Cooperation Treaty) and International Preliminary Report on Patentability for PCT/JP2006/302192 dated Aug. 23, 2007.

* cited by examiner

MEDICAL TRAINING MODEL DEVICE

This application is a National Stage Application of PCT/JP2006/302192, filed Feb. 8, 2006, which claims priority to JP 2005-032614 filed Feb. 9, 2005.

BACKGROUND OF THE INVENTION

1. Field of the Invention

The present invention relates to a teaching material model system capable of displaying the positional situation of a sensor for detecting signals from a specific signal transmitting means inside a teaching material organism model in real time and in a three-dimensional figure, the model being a teaching material model for clinical examination inside of organism.

2. Description of the Related Art

In medical fields, various types of endoscopes are in heavy usage on actual medical job sites, and palpation by fingers is also carried out frequently. For both, it is required to be strictly trained to learn techniques. In addition, in a maieutic field also, for defending the security of mother and child, reliable knowledge and technique are indispensable, and carrying out sufficient training is requested. In particular, at childbirth, it is important to grasp situations that change moment by moment and have judgment and care that conform to the situation. For one method for grasping the course of the childbirth, there is an internal examination. However, since there is limitation on practicing an internal examination for an actual parturient in current education fields, training using an internal examination model is carried out.

In addition, for the training for livestock artificial insemination specialists, the exercise of livestock breeding for cattle, horse, swine, sheep, goat and the like is also necessary, but there is no appropriate model.

Thus, in actual conditions, the training for these is carried out on the basis of a simulation model that simulates the structure of an organism. However, according to traditional trainings based on a simulation model, it is difficult to grasp the position of an inserted endoscope, finger or the like, and, in addition, it is impossible to objectively recognize three dimensional positions in a tissue, therefore it is impossible to learn the combination of feeling and space recognition.

Conventionally, training models that combine a simulation model simulating the structure of an organism and a three-dimensional graphic display unit have been already known, but, since no position of the inserted matter was displayed on the three-dimensional graphic display unit, sufficient training can not be practiced.

SUMMARY OF THE INVENTION

Problems to be Resolved by the Invention

The problem to be solved by the present invention is to provide a medical training simulation model having a display enabling training by a simulation model simulating the structure of an organism, and objective and visual recognition of the three-dimensional position of an inserted endoscope, a finger or the like in an organ or tissue.

Means of Solving the Problems

The present invention solved the problem according to the following constitution.

1. A teaching material model system composed of a teaching material model for clinical examination inside of an organism, which comprises: a display screen creating means for creating the internal structure of an organism model formed of nonmagnetic material by three-dimensional CG on a display screen; a specific signal transmitting means; and a sensor for detecting a signal from the specific signal transmitting means as constituent means, wherein the signal generated from the specific signal transmitting means is detected by the sensor, the signal detected by the sensor is transmitted to create a display screen by the display screen creating means, and the system is provided with a real time display means for displaying the positional situation of the sensor created on the display screen for the internal structure of a teaching material organism model displayed on the display screen by three-dimensional CG.

2. The system according to preceding clause 1, wherein the organism model is at least one organ selected from the pelvis, the anus-colon segment, the esophagus, the stomach, the duodenum, the large intestine, the small intestine, the colon, the vagina, the cervical canal and the uterine cavity.

3. The system according to preceding clause 1 or 2, wherein the organism model is formed of a synthetic polymer material selected from silicone, vinyl chloride and polyurethane.

4. The system according to any one of preceding clauses 1 to 3, which comprises at least one sensor mounted on an intra-organ inserting means of the organism model.

5. The system according to preceding clause 4, wherein the sensor is used at the tip of at least two internal examination fingers in an internal examination model.

6. The system according to preceding clause 4, wherein the sensor is used at the tip portion of an endoscope.

7. The system according to any one of preceding clauses 4 to 6, wherein the three-dimensional CG is created so that at least the three dimension of the figure of the intra-organ inserting means can be differentiated, which is displayed in conjunction with the intra-organ inserting means in the three-dimensional CG on the display screen creating means of the internal structure of the organism model.

8. The system according to any one of preceding clauses 1 to 7, wherein the display screen is stored in a memory means to allow replay, adjustment and correction thereof.

Advantage of the Invention

In the present invention, by using a simulation model that simulates the structure of an organism, displaying portions that can not be checked visually by means of three-dimensional graphics, and using a magnetic sensor for an intruding matter, an operator can grasp the position and movement of such intruding matter as an endoscope or finger on three-dimensional graphics in real time.

DESCRIPTION OF NUMERALS

Figure 1A:
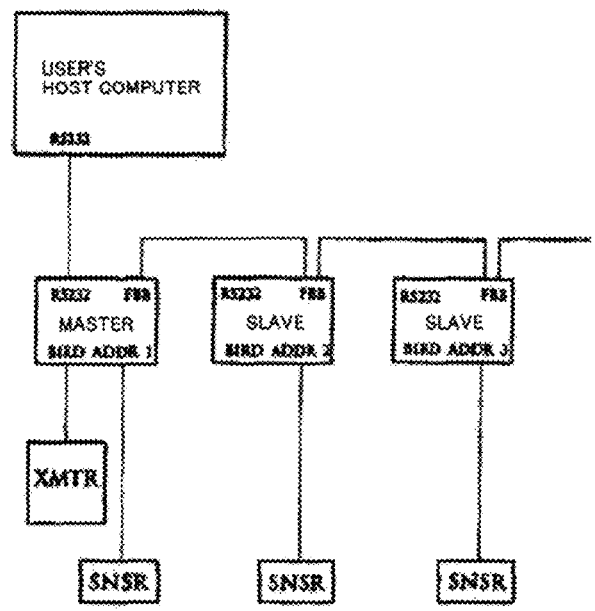
FIG. 1A is a series connection diagram, showing series connection to a host computer by a single RS232 interface.

1: transmitter
2: intra-organ inserting means
3: organism model

4: CG of internal examination fingers
5: CG of uterus of an organism model
XMTR: transmitter
SNSR: sensor

DESCRIPTION OF THE PREFERRED EMBODIMENTS

An object of the present invention is a teaching material model for clinical examination inside of an organism. Many such models have been already offered commercially, including, for example, the pelvis, the anus-colon segment, the esophagus, the stomach, the duodenum, the large intestine, the small intestine, the colon, the vagina, the cervical canal, the uterine cavity and the like. In the present invention, these models must be formed of a nonmagnetic material. This is because a magnetic sensor is used for a sensor that detects signals from a specific signal transmitting means and the material is inevitably nonmagnetic. For the material, preferred are those which are easily formed, elastic, and have physical properties equivalent or similar to those of an organism. Accordingly, the organism model is formed of a synthetic polymer material selected from silicone, vinyl chloride and polyurethane. In the present invention, as to the sensor, a touch sensor, a pressure sensor or the like can not follow a three-dimensional position and movement. In addition, for a sensor having such size that gives no uncomfortable feeling to diagnostic manipulation when being mounted on a finger or the like, a magnetic sensor is optimum.

The specific signal transmitting means and a detection means including a sensor for detecting the signal are constituted of a transmitter, a sensor and a controller, and detects by the sensor magnetic information (specific signal) generated from a transmitter being a specific signal transmitting means, and the signal is displayed by a display screen creating means to create such display screen as a monitor display. Both the transmitter and the sensor are connected to a controller by a cable, and, from the controller, they are connected to a card thrust into PCI bus of a personal computer. When plural sensors are used, this constitutional unit is required by the number of the sensor sets. There are two ways for connecting respective sets, which are shown in the drawing. Such type of a magnetic sensor that is connected to USB other than PCI bus may be also used. Incidentally, the card for PCI bus has three connectors for connecting with the controller.

The signal detected by the sensor is displayed in the three-dimensional CG by the display screen creating means of the internal structure of the organism model, which has been set previously, making it possible to display the positional situation of the sensor inside the teaching material organism model in real time. For the three-dimensional CG of the internal structure of the organism model, one that is similar to an actual internal examination model is used. Consequently, the three-dimensional CG of the internal structure of the organism model is corrected by means of fixed point measurement or the like.

By moving the sensor in front of the transmitter, the finger on the screen moves smoothly, and by rotating the sensor, the direction of the finger is also rotated. In addition, the relation between the image of the finger and that of such organism model as the pelvis is displayed well. When the finger goes to the rear side of such organism model as the pelvis, the display is carried out so that a part of the finger is hidden by the pelvis as if the finger had gone to the rear side of the pelvis.

There is at least one sensor for detecting the signal, and plural ones are effective for grasping more complex positional relation. Specifically, in the case of an internal examination model for example, there is shown such instance as total two sensors, where each one sensor is set on the nail side tip of two internal examination fingers (forefinger and middle finger). For an endoscope, a sensor is used at the tip portion thereof. The sensor is mounted on, for example, an intra-organ inserting means. There is no limitation on the intra-organ inserting means when it is such means or an instrument as a finger or an endoscope that carries out treatment in organs that can not be viewed visually. For the magnetic sensor, any magnetic sensor may be used insofar as it can display a position three-dimensionally and has a small size. Specifically, MiniBird from Ascension Corporation can be mentioned. These magnetic sensors can detect within a range of around 1.5 to 2 m in diameter, usually, to allow three-dimensional CG within the range to be displayed.

Then, three-dimensional CG that can preferably rotate so that at least the three-dimensional figure of the intra-organ inserting means can be discriminated is formed, which is displayed in conjunction with the movement of the intra-organ inserting means in three-dimensional CG of the organism model on the display screen creating means.

In the present invention, for the screen image created on a display screen, storing treatment is possible, and, replay, adjustment and correction thereof are possible. This is a means that makes it possible to check later the own movement for a person subjected to training after importing the data, or to display desirable movement of a finger separately.

Figure 1B:
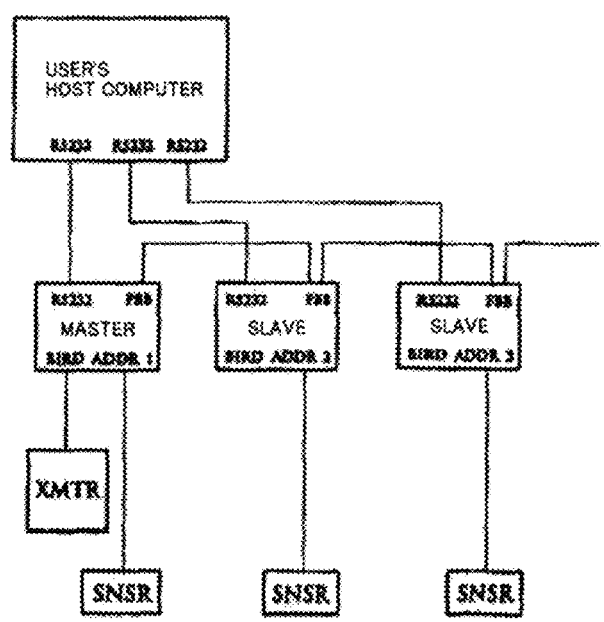
FIG. 1B is a parallel connection diagram, showing parallel connection to a host computer individually by a single RS232 interface.
Figure 2:
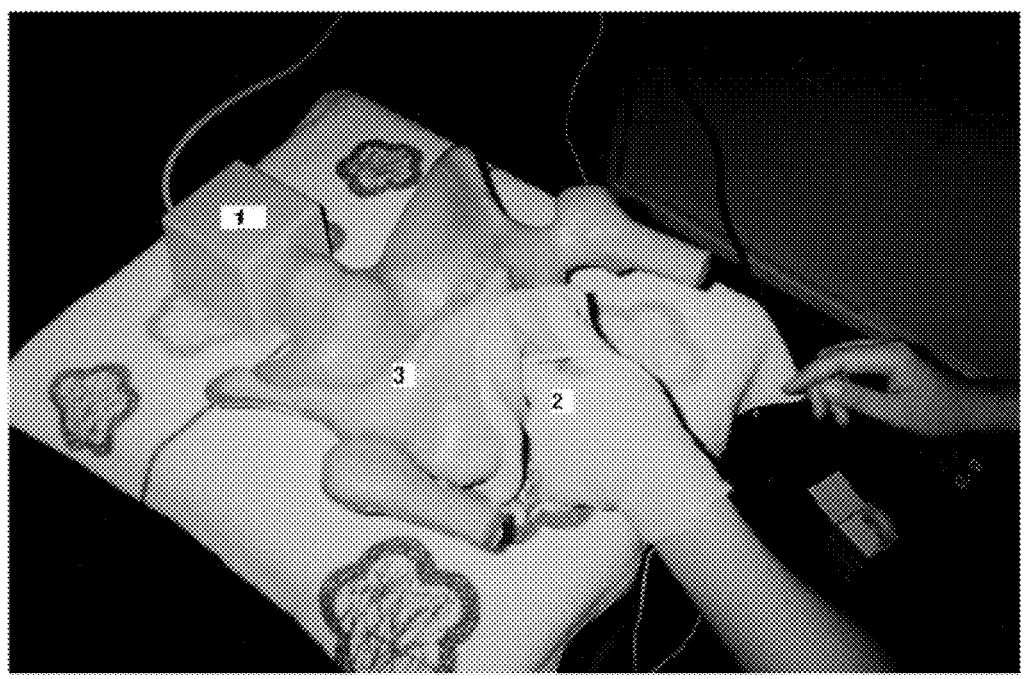
FIG. 2 is a drawing showing a use situation.

FIGS. 1-1 and 1-2 are diagrams that show a series connection and a parallel connection of a transmitter (specific signal transmitting means), sensors for detecting the signal from the transmitter, and a master device (master) and slave devices (slave) for displaying three-dimensional CG to display the specific signal in the CG. The former has simple connection and high versatility, but the increase in the number of the sensors generates problem in transmission speed. In the latter, the transmission speed is maintained constant irrespective of the number of the sensors, but the connection becomes complex.

FIG. 2 shows a specific use situation, wherein numeral 1 is a transmitter, numeral 3 is an organism model, and numeral 2 is an intra-organ inserting means, which is a finger specifically. On the nail side tip of the forefinger and the middle finger among the fingers, each one sensor is mounted. In the drawing, two inserted fingers touch the uterine os to evaluate the position and the open of the uterine os. The wire extending backward from the detection means is a connection line with a monitor display and a computer.

Figure 3:
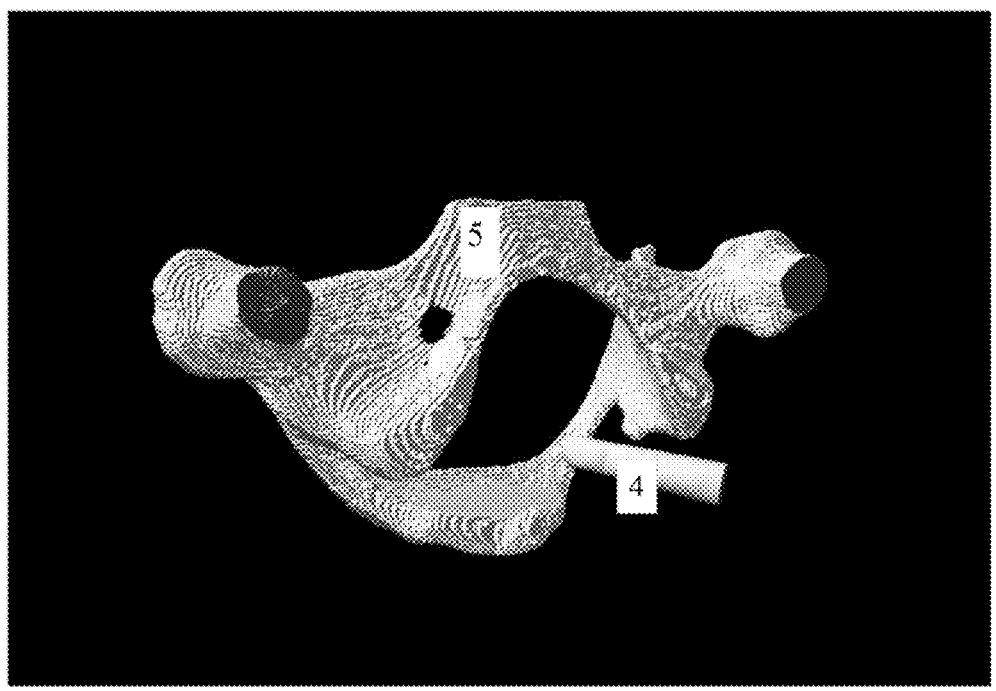
FIG. 3 is a drawing showing CG.

FIG. 3 is an organism model displayed as CG, which is a CG drawing of a model for the inside of the uterus. In the drawing, numeral 4 is three-dimensional CG of the figure of the forefinger as an internal examination finger down to the second knuckle so formed that the nail side and the bulb side of the finger can be discriminated, and shows an internal examination finger CG in conjunction with the movement of the finger. Numeral 5 is a drawing that shows CG of the inside of the organism model uterus.

EXAMPLE

When the system of the present invention is practiced, the flow of data processing is as follows.

1) Preparation of Three-Dimensional Model Data (the Pelvis Data etc.)

In the present system, three-dimensional data of the teaching material model being the actual teaching material model for clinical examination inside of an organism are previously prepared, which are displayed on the display screen creating means as three-dimensional CG. For the data of actual teaching material model, in the case of an organism, from a three-dimensional image imported through CT scan or MRI, a three-dimensional model, that is, three-dimensional CG is established by using equivalent-face processing or segmentation technique. The teaching material model is previously modeled by using a geometric modeling software.

2) Preparation of Three-Dimensional Data for the Figure of the Intra-Organ Inserting Means (Internal Examination Finger, Endoscope etc.)

The data for the inserting means (hereinafter, referred to as "inserting terminal") into the organ of a teaching material model, for example an internal examination finger, an endoscope or the like are previously arranged, which are prepared as three-dimensional CG (for example, internal examination finger CG).

Such three-dimensional model data as described above (that is, three-dimensional CG) is composed of the assemblage of polygons, and each of the polygons is composed of vertex coordinates and vertex strings connecting the coordinates, wherein the vertex strings are arranged in a predetermined alignment (for example, anticlockwise direction).

3) Usage Embodiment

A user is trained by inserting an inserting terminal into the organ of an actual teaching material model. The movement of the inserting terminal in the organ is invisible for the user, and grasping the position and movement is difficult. But, by providing the inserting terminal with a three-dimensional sensor, the user can grasp, in real time, the position and the movement of the teaching material model and the inserting terminal by means of three-dimensional CG in conjunction with the actual movement of the inserting terminal.

4) Input Data from User

The user can adjust the relative position between an actual teaching material model and the inserting terminal when using the system. Since, in order to display accurately the model and the inserting terminal on a computer, adjustment is necessary according to need. When the teaching material model is completely fixed, the adjustment is however not necessary.

5) Import of Data from Three-Dimensional Model Positional Sensor

By a magnetic sensor provided to the inserting terminal, data for the position and direction (posture) are imported into a computer.

6) Calculation of Screen Synthesis

The information from a positional sensor (positional information and direction) and the three-dimensional model data have been defined in the same coordinate space. Further, by subjecting the display on the screen to expansion-contraction conversion, the actual movement and the movement on the screen are related. In other words, calculation for synthesizing three-dimensional model data (the pelvis data, etc.) and the data from the three-dimensional positional sensor on the screen is carried out on a computer.

7) Screen Output

Three-dimensional model data and the position of the inserting terminal user are synthesized on the screen in real time to be output on the screen as three-dimensional CG.

What is claimed is:

1. A teaching material model system composed of a teaching material model for clinical examination inside of an organism, which comprises: a display screen creating means for creating the internal structure of an organism model formed of nonmagnetic material by three-dimensional computer graphics on a display screen; a transmitter positioned remote from the organism model; and a magnetic sensor for detecting a signal from the transmitter, the magnetic sensor mounted on an intra-organ inserting means of the organism model, wherein the signal generated from the transmitter is detected by the magnetic sensor, the signal detected by the magnetic sensor is transmitted to create a display screen by the display screen creating means, the system is provided with a real time display means for displaying the positional situation of the magnetic sensor created on the display screen for the internal structure of a teaching material organism model displayed on the display screen by three-dimensional computer graphics, the three-dimensional computer graphics are created so that at least the three dimensions of the figure of the intra-organ inserting means are capable of being differentiated, which are displayed in conjunction with the intra-organ inserting means in the three-dimensional computer graphics on the display screen of the internal structure of the organism model, the organism model is at least one organ selected from the vagina, the cervical canal, and the uterine cavity, and the magnetic sensor is used at the tip of at least two internal examination fingers in an internal examination model.

2. The system according to claim 1, wherein the organism model is formed of a synthetic polymer material selected from silicone, vinyl chloride and polyurethane.

3. The system according to claim 1, wherein the display screen is stored in a memory means to allow replay, adjustment and correction thereof.

* * * * *